United States Patent
Novak et al.

(10) Patent No.: US 6,443,969 B1
(45) Date of Patent: Sep. 3, 2002

(54) ULTRASONIC CUTTING BLADE WITH COOLING

(75) Inventors: Theodore A. D. Novak, Kings Park; Sergio Portela DeAlbuquerque, Selden; Werner Sladek-Maharg, Coram, all of NY (US); Dan Voic, Clifton, NJ (US)

(73) Assignee: Misonix, Inc., Farmingdale, NY (US)

( * ) Notice: Subject to any disclaimer, the term of this patent is extended or adjusted under 35 U.S.C. 154(b) by 0 days.

(21) Appl. No.: 09/639,060

(22) Filed: Aug. 15, 2000

(51) Int. Cl.[7] .............................................. A16B 17/32
(52) U.S. Cl. ..................................................... 606/169
(58) Field of Search ........................... 606/1, 167, 169; 604/22; 30/515

(56) References Cited

U.S. PATENT DOCUMENTS

| | | |
|---|---|---|
| 878,524 A | 2/1908 | Gregory |
| 1,333,745 A | 3/1920 | Wescott |
| 2,845,072 A * | 7/1958 | Shafer ........................ 606/169 |
| 3,526,219 A | 9/1970 | Balamuth |
| 3,636,943 A | 1/1972 | Balamuth |
| 3,832,776 A | 9/1974 | Sawyer |
| 4,008,720 A | 2/1977 | Brinckmann |
| 4,667,408 A | 5/1987 | Kirk |
| 4,832,683 A * | 5/1989 | Idemoto et al. .............. 606/169 |
| 5,188,102 A | 2/1993 | Idemoto et al. |
| 5,261,922 A * | 11/1993 | Hood ........................... 604/22 |
| 5,322,055 A | 6/1994 | Davison et al. |
| 5,391,144 A | 2/1995 | Sakurai et al. |
| 5,674,235 A | 10/1997 | Parisi |
| 6,254,622 B1 * | 7/2001 | Hood ........................... 606/169 |

* cited by examiner

Primary Examiner—Ismael Izaguirre
(74) Attorney, Agent, or Firm—R. Neil Sudol; Henry Coleman; William Sapone (57) ABSTRACT

At an ultrasonic surgical blade has a blade body with a smooth continuous cutting edge and a shank connected at one end to the blade body and operatively connectable at an opposite end to a source of ultrasonic vibrations. The shank is provided with at an axially extending bore for the conveyance of cooling fluid to the cutting edge, while the blade body is provided with at an axially extending through-slot communicating at one end with the bore. The blade body is preferably provided at an end opposite the shank with a recess communicating with the bore for distributing fluid from the slot towards the cutting edge.

22 Claims, 8 Drawing Sheets

ULTRASONIC CUTTING BLADE WITH COOLING

FIELD OF THE INVENTION

This invention relates to an ultrasonic cutting blade. The blade is particularly useful in a surgical application to cut tissue such as cartilage and bone.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade which has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf; so that a significant thickness of the viable bone is lost in the cutting procedure. Physicians would like this width to be as thin as possible in most procedures where reconstruction is necessary.

Above all, the relatively slow linear or tangential speeds of conventional bone saw blades coupled with the teeth necessary for cutting result in high frictional losses, which becomes manifested as heat. Heat will cause necrosis of the tissue if the bone temperatures reach 47° C. for more than a few seconds. When tissue necroses, the bone recedes after the surgery as the necrotic bone is overgrown. During such natural post-surgical tissue developments, the thickness of the cuts in the bone actually increases. The bone rescission process must be complete before healing can begin. To prevent the shortening of the length of the bone, metal plates and screws are used to fix the bone fragments in proper position. All of these factors obviously lead to increased operative time, and more importantly, to dramatically increased healing time, since the bone must knit across a greater span. Some studies have shown the strength of the bone to be effected negatively as well When an upper or lower jaw is to be cut in elective surgery, the heating effect of traditional saws requires even more extraordinary intervention to prevent damage. Cutting the jaw between the teeth will cause loss of teeth if the bone is damaged or does not heal quickly. To prevent the tooth loss, the teeth must be spread apart preoperatively; sometimes forcing the patient to wear braces for up to 6 months before the operation can take place. In these cases, the costs and patient discomfort increases dramatically.

To limit the tissue temperature rise in an attempt to reduce necrosis, some traditional surgical saws provide cooling liquid to the surgical site. See, for instance, U.S. Pat. No. 4,008,720 to Brinckmann et al. These devices typically introduce coolant into spaces between segments on the cutting edge or rely on spray methods to flood the cutting site with fluid. Another technique employed by clinicians is to make very light cuts and increase the time between passes of the tool. Coupled with irrigation of the area, bone temperature rise is reduced measurably. Of course, this technique increases operative time and clinician fatigue.

Several researchers have proposed the use of ultrasonic tools for bone separation. The use of ultrasonic surgical instruments for cutting through various tissues is well known. While these devices are superior to the traditional saws in several aspects such as reduced kerf size, reduced noise, and superior ability for making complex geometric cuts, the temperature rise in bone due to frictional heating at the blade/tissue interface is still a significant problem. The problem is exacerbated with the use of ultrasonics due to the rapid motion involved as compared to that of traditional reciprocating saws. Some designers have tried to reduce heating by modifying the cross-section of the cutting blade. U.S. Pat. No. 5,188,102 to Idemoto, U.S. Pat. No. 4,188,952 to Loschilov, and U.S. Pat. No. 5,261,922 to Hood all show designs for cutting which have modified cross sections to reduce frictional heating.

Several ultrasonic devices have provided cooling to the cutting blade with varied degrees of success. U.S. Pat. No. 4,823,790 to Alperovich et al. shows a design for a cryogenically cooled scalpel blade. However, this design may actually damage viable tissue by freezing. In addition, this design does not provide any coolant to surrounding tissue not in direct contact with the blade.

U.S. Pat. Nos. 5,205,817, 5,188,102, and 4,832,683 all to Idemoto show examples of ultrasonic instruments with provisions for fluid cooling. These instruments, however, either do not provide optimal coolant flow where it is needed, mainly at the cutting portion of the blade, or for ones that do provide coolant at the tip, they interrupt the cutting edge with holes for the coolant. An interrupted, uneven cutting edge hinders manipulation and makes it difficult to guide the blade on the bone surface.

One phenomenon associated with ultrasonic tooling which acts to hinder the beneficial effects of irrigating the operative site is ultrasonic atomization. When an ultrasonically vibrating body is brought into contact with fluid, that fluid is broken into small droplets which have a size inversely proportional to the frequency of vibration. In other words, the higher the frequency, the smaller and more mobile the liquid drop. Droplets created by ultrasonic vibrations can be very small in size, with some being less than 1 micron in diameter. This phenomenon is well known to the art. In fact, many devices intended to atomize liquid, such as room humidifiers, medical nebulizers, and industrial spray nozzle are based upon this principle. In the operating theater, however, the presence of nebulized particles is not appreciated, since these particles may contain viral or bacterial agents. Also, some of the fluid will be atomized before reaching the operative site, reducing the cooling efficiency. An effective way to insure the liquid transport is needed.

SUMMARY OF THE INVENTION

The present invention recognizes the need which exists for an improved blade for use with ultrasonic cutting instruments. The invention is directed to an ultrasonic cutting blade which allows thin kerf cuts, does not require predrilled holes for cutting, allows complex geometric cuts, has a continuous cutting surface, and provides for liquid irrigation at primarily the blade/tissue interface. More specifically, the present invention pertains to an ultrasonically vibrated cutting blade with a provision for delivery of a cooling medium for reducing and limiting thermal damage to living tissue. The present invention specifically targets the application of cutting viable bones in surgery, although the device is not exclusive to this application.

An ultrasonic surgical blade in accordance with the present invention comprises a blade body having a smoothly continuous cutting edge and further comprises a shank connected at one end to the blade body and operatively connectable at an opposite end to a source of ultrasonic vibrations.

Preferably, the cutting edge is disposed in a single plane and has an arcuate section. The arcuate section is substantially circular and is disposed on the blade body opposite the shank. The cutting edge might additionally include a pair of straight sections continuous with the circular section at opposite ends thereof. Where the blade body has a longitudinal axis, the straight sections are oriented substantially parallel to the axis.

In accordance with another feature of the present invention, the shank is provided with an axially extending bore for the conveyance of cooling fluid to the cutting edge, while the blade body is provided with an axially extending through-slot communicating at one end with the bore. The blade body is preferably provided at an end opposite the shank with a recess communicating with the bore for distributing fluid from the slot towards the cutting edge. The recess preferably has a configuration which parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

Where the fluid distribution guide surface is an inclined surface extending between the passageway or bore and the cutting edge.

The basic advantages derived from the present invention are as follows. The blade edge is continuous, i.e., having no teeth, serrations or voids. This continuity provides a smooth contact surface essential when making precise cuts. In contrast, in an ultrasonic cutting blade having teeth, serrations or interruptions, the feel of the instrument changes and the instrument is more difficult to guide as the teeth, serrations, or interruptions are moved across the bone at the surgical site. Teeth on the blade edge not only do not improve the cutting speed but make it difficult to keep the edge on a predetermined cut line. The continuous blade edge of the present invention also gives the cutting process a consistent feel to the surgeon, similar to the feel of a standard scalpel blade.

Another advantage of the present ultrasonic instrument is the structure within the blade for providing irrigation to the blade edge. Experimentation has shown that atomization is substantially reduced. Additionally the coolant fluid is delivered along the side of the blade and into the cut, but the delivery mechanism does not interrupt the cutting edge as has been found to be significant in the instrument's feel and performance, The advantages to this invention beyond its use are in its predicted results there will be less dead bone and a small cut width. This keeps the cut narrow and provides for quicker healing than if the bone were overheated to necrosis or if the cut was wider.

DETAILED DESCRIPTION OF THE INVENTION

Figure 1:
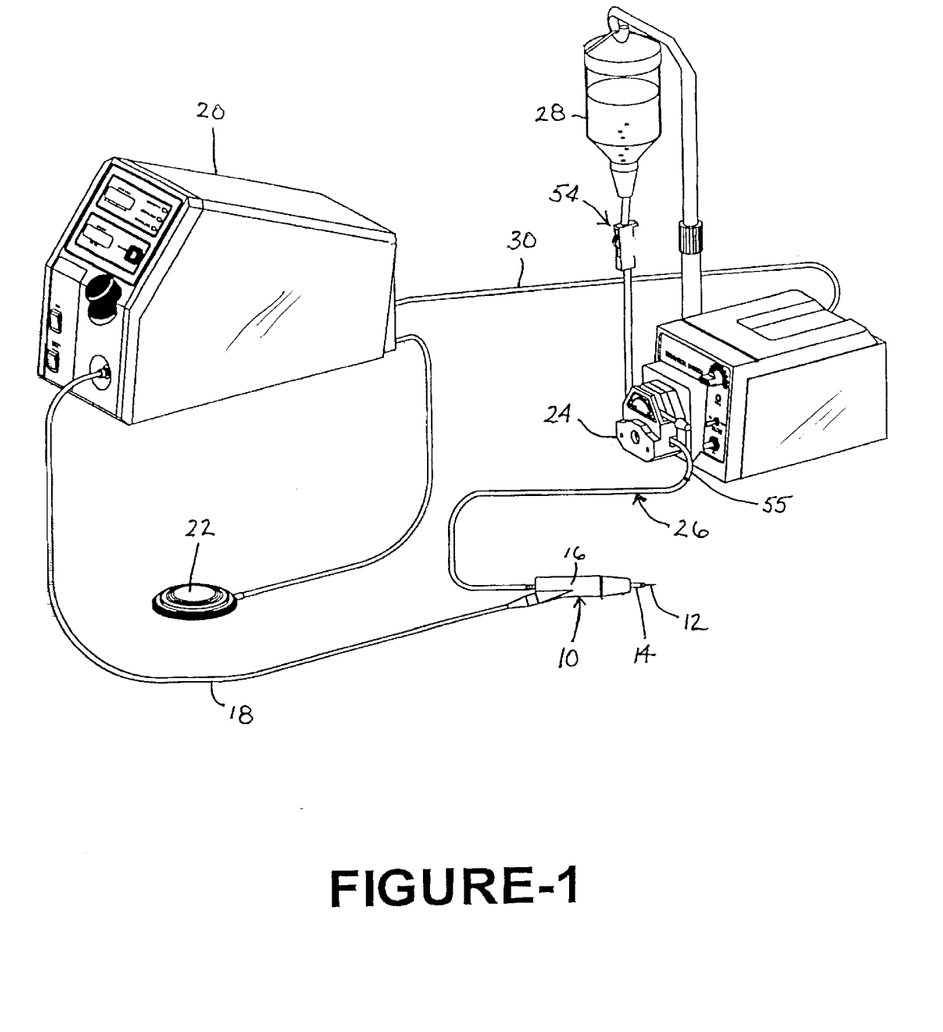
FIG. 1 is an overall view of a surgical system having ail ultrasonic cutting blade in accordance with the present invention.

As shown in FIG. 1, an ultrasonic surgical system includes a handpiece 10 carrying a cutting blade 12. Handpiece 10 is attached to blade 12 via a probe 14 and further includes a housing 16 which encases a piezoelectric crystal assembly of the kind disclosed in U.S. Pat. No. 5,371,429 to Manna. In response to a sinusoidal oscillating signal transmitted over a cable 18 from an ultrasonic generator 20, the crystal assembly in the probe produces longitudinal ultrasonic pressure waves transmitted through probe 14 to blade 12. Signal generator 20 is activated via a footswitch 22. Handpiece 10 is also connected to an irrigation pump 24 via a tube 26. Pump 24 moves an irrigant liquid from a reservoir or IV type hanging bag 28 through tube 26 to handpiece 10 in response to a signal carried over a cable 30 from signal generator 20 under the control of footswitch 22.

The mechanical vibration produced by the piezoelectric crystal assembly in handpiece 10 is amplified mechanically via the transducer shape and still further by the shape of probe 14 and blade 12, using techniques known to those skilled in the art of ultrasonics. Probe 14 is attached to handpiece 10 via an externally threaded connection 31, shown in FIG. 2. Probe 14 is thus replaceable by the user to facilitate the use of disposable sterile blades 12 from one procedure to the next. Handpiece 10 may be sterilized by autoclaving as well as by other conventional methods. While probe 14 can be sterilized, maintaining a good cutting edge and cleanliness is such a key issue that a disposable tip or a disposable probe/tip assembly is envisioned. The primary purpose of probe 14 is to mechanically amplify the vibration from the piezoelectric transducer assembly and transmit that vibration through to cutting blade 12.

Figure 3:
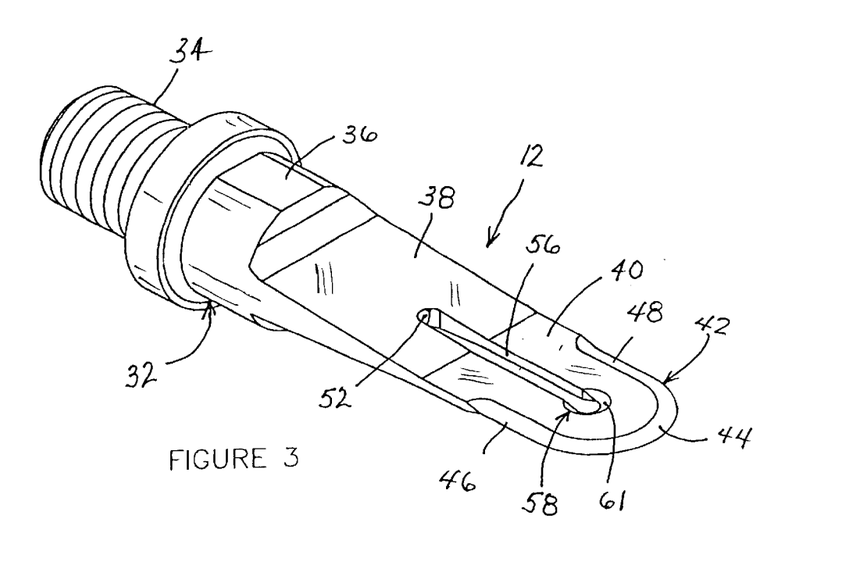
FIG. 3 is a perspective view, on an enlarged scale, showing the blade of FIG. 2 and a blade shank.
Figure 4:
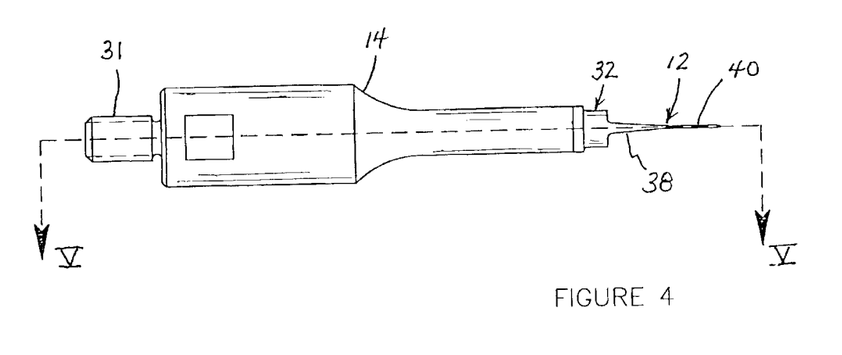
FIG. 4 is a side elevational view of the probe and blade of FIG. 2.
Figure 5:
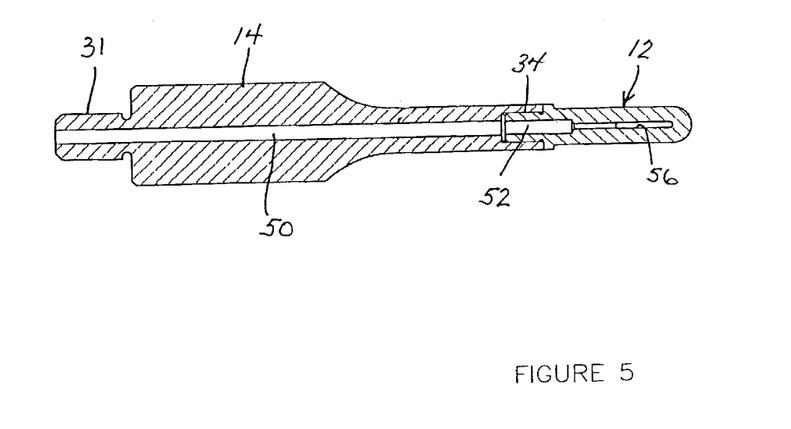
FIG. 5 is a longitudinal or axial cross-sectional view taken along line V—V in FIG. 4.
Figure 6:
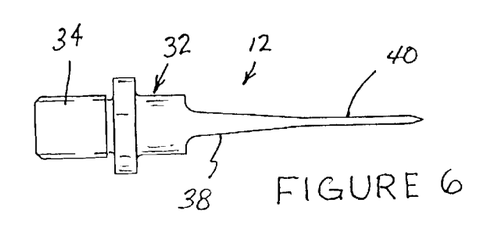
FIG. 6 is side elevational view of the cutting blade of FIGS. 2–5.

As illustrated in FIG. 3, cutting blade 12 includes an integral shank portion 32 having an external screw thread 34 for replaceably mounting the blade to probe 14. Alternatively, blade 12 may be permanently attached to probe 14. In the former case, blade 12 is tightened by a wrench (not shown) applied to wrench flats 36 on shank portion 32. Blade 12 is shaped to amplify the longitudinal vibratory motion. More specifically, blade 12 includes a tapered or wedge-shaped portion 38 connected to shank portion 32 for focusing or concentrating ultrasonic vibratory energy and transmitting the energy to a planar portion 40 of blade 12. The whole transducer, horn and tip assembly is designed to resonate in a longitudinal or back and forth type of motion. This motion provides the cutting action at the tip of blade 12.

Planar blade portion 40 is provided at an end opposite tapered portion 38 and shank 32 with a blade edge 42 including a central circularly arcuate section 44 and a pair of linear end sections 46 and 48. Blade or cutting edge 44 is sharpened along a full radius of arcuate section 44, as well as along straight sections 46 and 48, with a knife type edge that can smoothly be drawn back and forth in a brushing type motion. This cutting edge structure allows the user to maintain a constant motion at the tip, which has been shown to be important to prevent overheating of the tissue at the surgical site.

As further illustrated in FIGS. 3, 5, 7, 9, and 10, blade 12 also incorporates structure providing a path for coolant from irrigation pump 24 (FIG. 1) to reach blade edge 42, as well as tissues being cut during a surgical procedure. For conducting irrigant to blade edge 42 and the surgical site, probe 14 is formed with an axial passageway or bore 50 (FIGS. 5 and 10) which communicates with an axial passageway or bore 52 in blade 12 and more particularly in shank 32 and part of tapered blade portion 38. The irrigation fluid is typically a sterile saline solution supplied in hanging bag 28 (FIG. 1). Bag 28 is punctured with a vented IV spike supplied at the end of a sterile tube set 54. The spike allows the fluid to flow into a silicone tube section 55 of tube 26 of set 54. Silicone tube section 55 passes through pump 24 which takes the form of a peristaltic or roller type pump. Pump 24 pushes the fluid along tube 26 to a connection at the handpiece 10. The fluid travels through an integral channel inside the handpiece 10, as described in U.S. Pat. No. 5,371,429. From handpiece 10 the fluid travels through probe 14 to blade 12.

Figure 2:
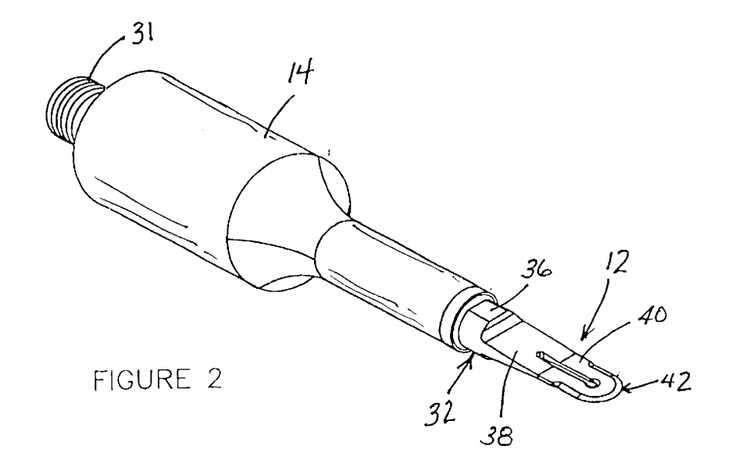
FIG. 2 is a perspective view of an ultrasonic probe and an associated ultrasonic blade in accordance with the invention.
Figure 7:
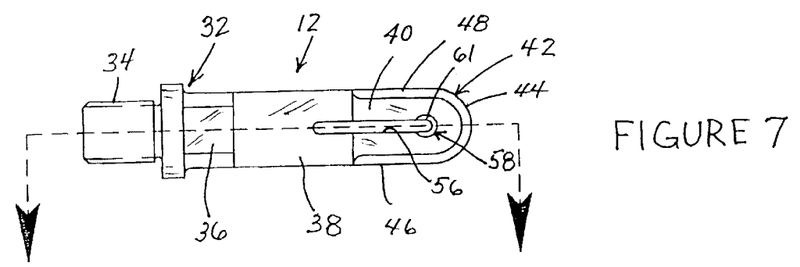
FIG. 7 is a top plan view of the cutting blade of FIGS. 2–6.
Figure 8:
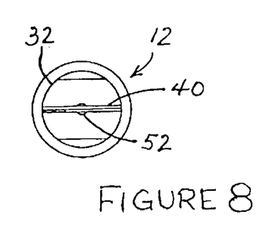
FIG. 8 is a front elevational view of the cutting blade of FIGS. 2–7.
Figure 9:
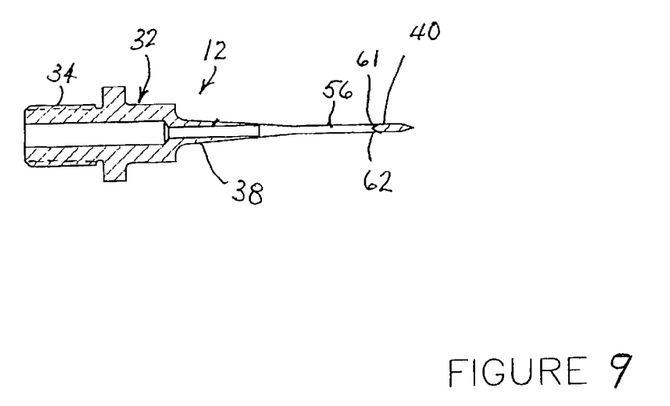
FIG. 9 is a cross-sectional view taken along line IX—IX in FIG. 7.
Figure 10:
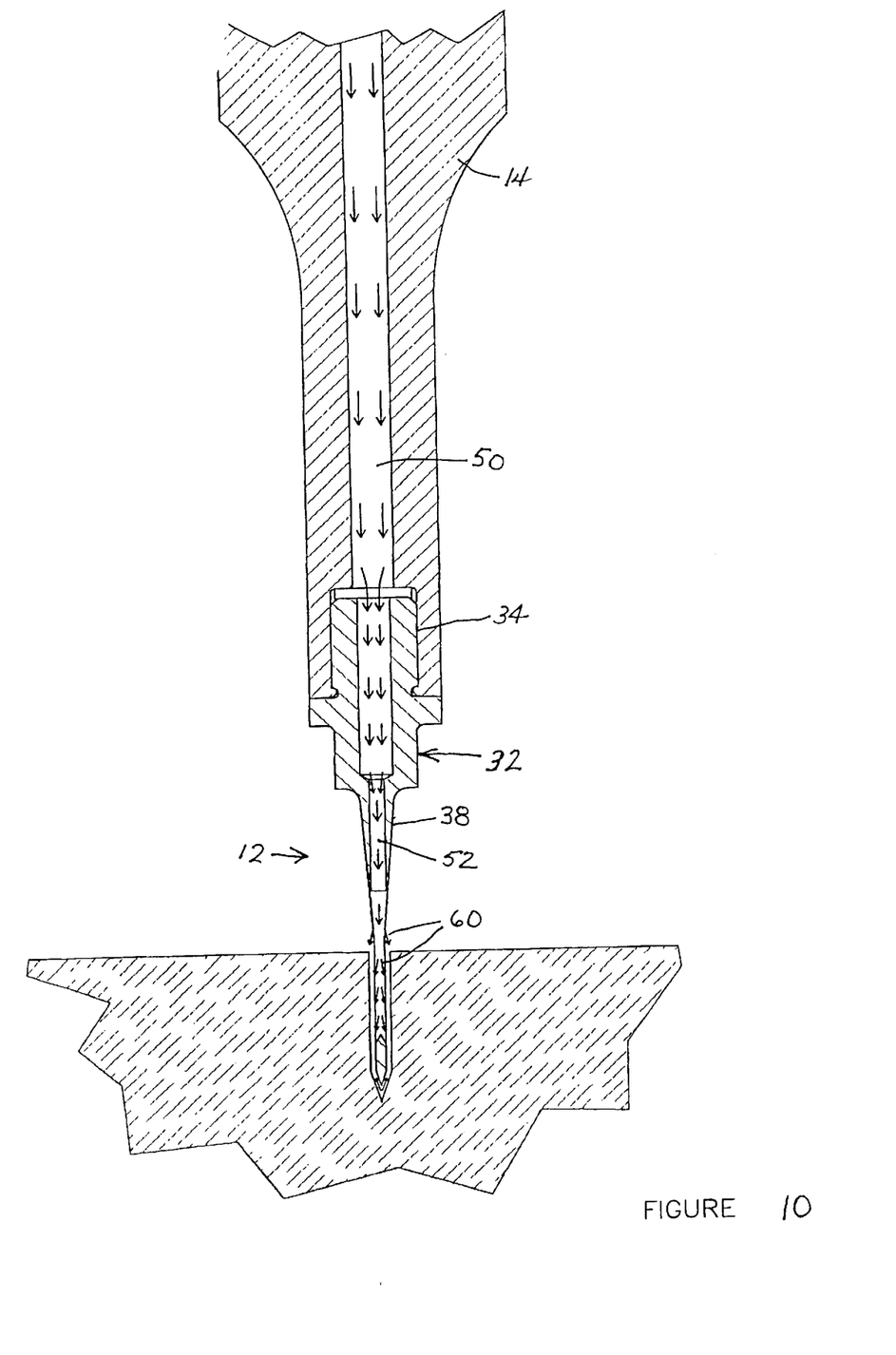
FIG. 10 is a longitudinal cross-sectional view of a portion of the probe and the blade of FIGS. 2, 4, and 5, with arrows indicating a flow path of irrigant.

Passageway or bore 52 terminates in an open longitudinal channel or slot 56 that enables the coolant to spread out and onto the planar portion 40 of blade 12. This open channel or slot 56 is an important feature when blade 12 is located deep in a cut because the channel or slot distributes irrigant all along the sides or lateral surfaces of planar blade portion 40 and not in only specific locations, as indicated by arrows 60 in FIG. 10. At an end of channel or slot 56 opposite passageway or bore 52 is disposed a recess 58 in planar blade portion 40, as shown in FIGS. 2, 3, and 7. Recess 58 has an arcuate or, more specifically, circular, configuration (see FIG. 7) optionally concentric with that of arcuate blade edge section 44. Recess 58 is defined in part by a pair of inclined surfaces 61 and 62 (FIG. 9) for distributing irrigant from channel or slot 56 towards blade 40 and then to circular central blade section 44, along the length thereof. The fluid traveling down channel or slot 56 will encounter inclined surfaces 60 and 62 of recess 58 which exhibit an incident angle that deflects the fluid into the cut (FIG. 10) while minimizing splash back. Surfaces 60 and 60 may be planar, convex or concave.

The resonant portions of the transducer and probe 14 are typically made of a low acoustic loss material that should also be biocompatible. Titanium 6AL4V alloy is the preferred choice but other alloys may be acceptable. Blade 12 may be constructed either of Titanium 6AL4V or Stainless Steel 17-4PH alloy. The latter material has a lower acoustic loss when compared to other stainless steels yet is robust enough to machine and hold an edge with the required geometry versus other stainless steel materials. If blade 12 and horn or probe 14 are made in one continuous piece either the stainless steel or the titanium alloy may be used.

To operate the system of FIG. 1, blade edge 42 is brought into contact with the intended surgical site. The system is activated via footswitch 22, the pressing of which causes ultrasonic generator 20 and irrigation pump 24 to operate. The ultrasonic signal from the generator 20 is transformed via the piezoelectric transducer crystals (not shown) in handpiece 10 into a mechanical vibration. This vibration is amplified and coupled from the transducer assembly to probe 14 and to blade 12. The vibrations at blade edge 42 perform the cutting and separation of bone tissue at the surgical site.

Blade edge 42 is moved back and forth in a brushing type of movement to keep the tip in motion. This cutting technique reduces the dwell time in any given location, which aids in minimizing any temperature rise at the surgical site. A continuous moving of the blade tip or edge 42 also prevents the blade from blocking the conveyance of irrigant fluid to any given spot and allows the irrigation fluid an opportunity to flow to that area. The smooth continuous blade edges 44, 46, 48 make it easier for the user to keep the blade 12 in motion and to keep it on a preselected cut line or track at the surgical site. Serrations, teeth, protrusions or indentations which are generally provided on other ultrasonic surgical blades hinder this mode of operation since the irregular surface causes the blade to drag and impedes the guiding of the blade. The ultrasonic vibrations also facilitate movement of blade 12 on the tissue surfaces at the surgical site since the vibrating blade breaks contact with the tissue on each vibratory cycle.

When the edge 42 of blade 12 begins to penetrate below the surface of the tissue, channel or slot 56 becomes particularly beneficial. During the initial phase of a surgical cutting procedure, channel or slot 56 only guides the fluid toward cutting edge 42. Subsequently, where blade edge 42 but not recess 58 is below the tissue surface, the recess design allows the irrigation fluid to flow down to the tip of blade 12 and helps to distribute the fluid across or along the blade edge. During a further stage of a surgical cutting operation, when recess 58 is located below the outer tissue surface, channel or slot 56 allows the irrigation fluid to flow out on both sides or lateral surfaces (not separately designated) of blade 12 and along the full length of the blade. This process provides cooling irrigation and lubrication to reduce the frictional heating on the sides of the blade.

The pressure on blade 12, particularly on blade edge 42 and planar blade portion 40, is also a significant factor in controlling the temperature at the surgical site. It has been determined that the pressure applied to blade 12 should be light, like writing with a pencil, not heavy as many surgeons have become used to with other bone cutting instruments.

While the irrigation is used for cooling, the coolant solution need not be chilled. Room temperature (18° C.) fluid has been shown to be adequate to cool the surgical site during an ultrasonic cutting operation with blade 12. This is, of course, more convenient and facilitates keeping extra fluid ready without concern for keeping it refrigerated. An exemplary flow rate is approximately 100 cc/min.

FIGS. 11–15 depict another ultrasonic cutting blade 64 utilizable in the system of FIG. 1. Cutting blade 64 includes an integral shank portion 66 having an external screw thread 68 for replaceably mounting the blade to probe 14. Alternatively, blade 64 may be permanently attached to probe 14. Blade 64 is shaped to amplify the longitudinal vibratory motion. More specifically, blade 64 includes a tapered or wedge-shaped portion 70 connected to shank portion 66 for focusing or concentrating ultrasonic vibratory energy and transmitting the energy to a planar portion 72 of blade 64.

Planar blade portion 72 is provided at an end opposite tapered portion 70 and shank 66 with a blade edge 74 including a central circularly arcuate section 76 and a pair of linear end sections 78 and 80 each of which extends at an acute angle relative to a longitudinal axis of the blade and which therefore extend at double that angle relative to one another. Blade or cutting edge 76 is sharpened along a full radius of arcuate section 76, as well as along straight sections 78 and 80, with a knife type edge that can smoothly be drawn back and forth in a brushing type motion.

Figure 13:
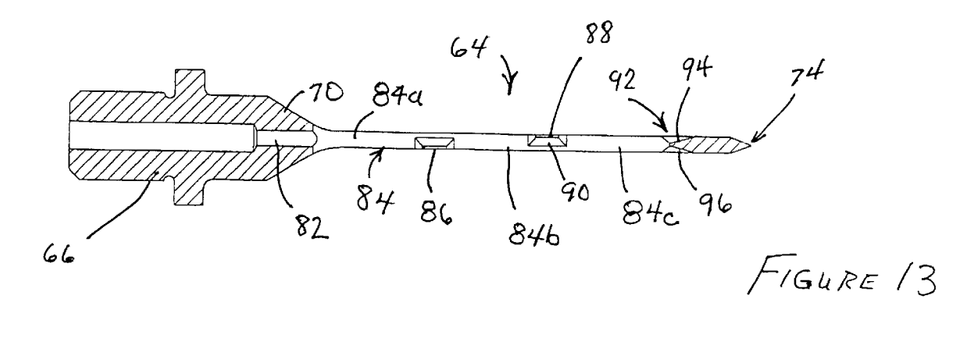
FIG. 13 is a longitudinal cross-sectional view of the blade of FIGS. 11 and 12, on a smaller scale, taken along line XIII—XIII in FIG. 11.
Figure 14:
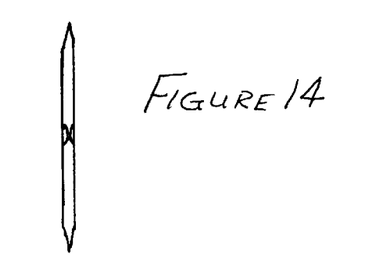
FIG. 14 is a schematic transverse cross-sectional view of the blade of FIGS. 11–13, taken along line XIV—XIV in FIG. 11.
Figure 15:
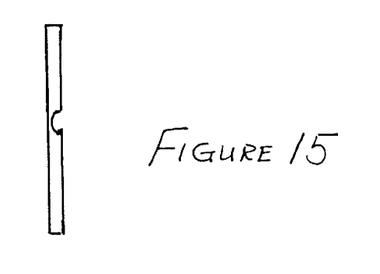
FIG. 15 is a schematic transverse cross-sectional view of the blade of FIGS. 11–13, taken along line XV—XV in FIG. 11.

As illustrated particularly in FIG. 13, for conducting irrigant to blade edge 74 and the surgical site, shank 66 is formed with an axial passageway or bore 82 which communicates with a segmented open longitudinal channel or slot 84 that enables the coolant to spread out and onto the planar portion 72 of blade 64. This open channel or slot 84 is divided into slot segments 84a, 84b, 84c by a pair of web sections 86 and 88 which bridge opposite sides of the channel or slot 84. As shown in FIG. 15, web sections 86 and 88 each define a respective recess, groove or passageway 90 (only one shown) disposed between the respective flanking slot segments 84a, 84b or 84b, 84c. These recesses, grooves or passageways 90 face in opposite directions and concomitantly communicate with opposing lateral faces (not separately designated) of planar blade portion 72.

At an end of channel or slot 84 opposite passageway or bore 82 is disposed a recess 92 in planar blade portion 72. Recess 92 has a conical or tapered cylindrical configuration. Recess 92 is defined in part by a pair of inclined surfaces 94 and 96 (FIG. 13) for distributing irrigant from channel or slot 84 towards blade 72 and then to circular central blade section 76, along the length thereof. The fluid traveling down channel or slot 84 will encounter inclined surfaces 94 and 96 of recess 92 and be deflected into the cut (FIG. 10) while minimizing splash back.

Cutting blade 64 is made of materials referred to above and operates in a manner described above. Blade 64 is considered to exhibit several improvements over blade 12. The greater length of blade 64 relative to blade 12 has the advantage of being able to cut completely through both cortical surface of a bone from one side. An equivalent cut using the shorter blade 12 requires cutting all around the bone in order to sever the bone. Such a procedure is not possible, for instance, in maxiofacial surgery on the mandibular bone.

The conical or tapered cylindrical shape of each surface 94, 96 of fluid distribution recess 92 makes blade 64 more robust and may be integrated into blade 12.

Web sections 86 and 88 stabilize blade 64 and thus facilitate or enable its greater length. Web sections 86 and 88 help reduce vibration noise during cutting and help increase the cutting performance of blade 64. Web sections 86 and 88 are each flush with a respective side of planar blade portion 72 and open or recessed (90) on the other side of planar blade portion 72. The fact that the web sections 86 and 88 face or open in opposite directions facilitates manufacturing and keeps the blade 64 balanced during ultrasonic excitation. The water slot web sections 86 and 88 also permit blade portion 72 to have a thinner cross-section, which accelerates the cutting of bone tissue and results in a thinner kerf.

Figure 11:
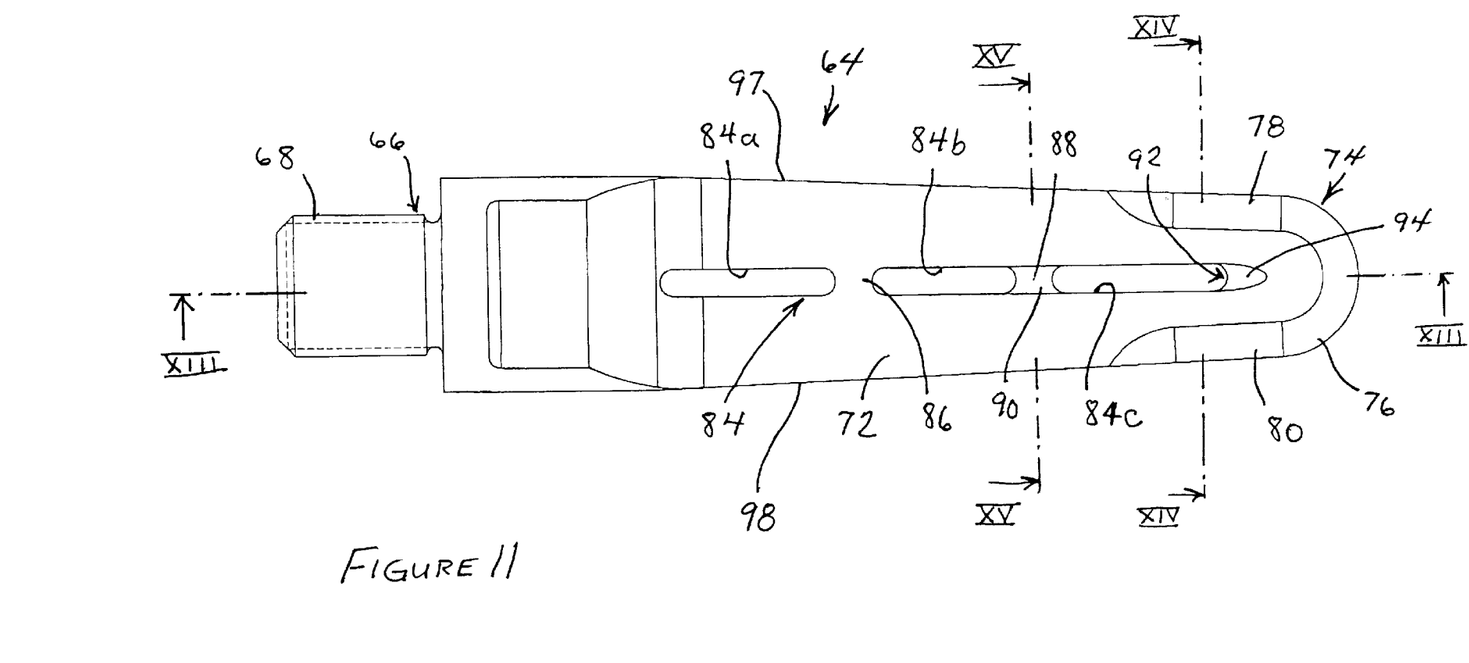
FIG. 11 is a top plan view of another ultrasonic cutting blade in accordance with the present invention.
Figure 12:
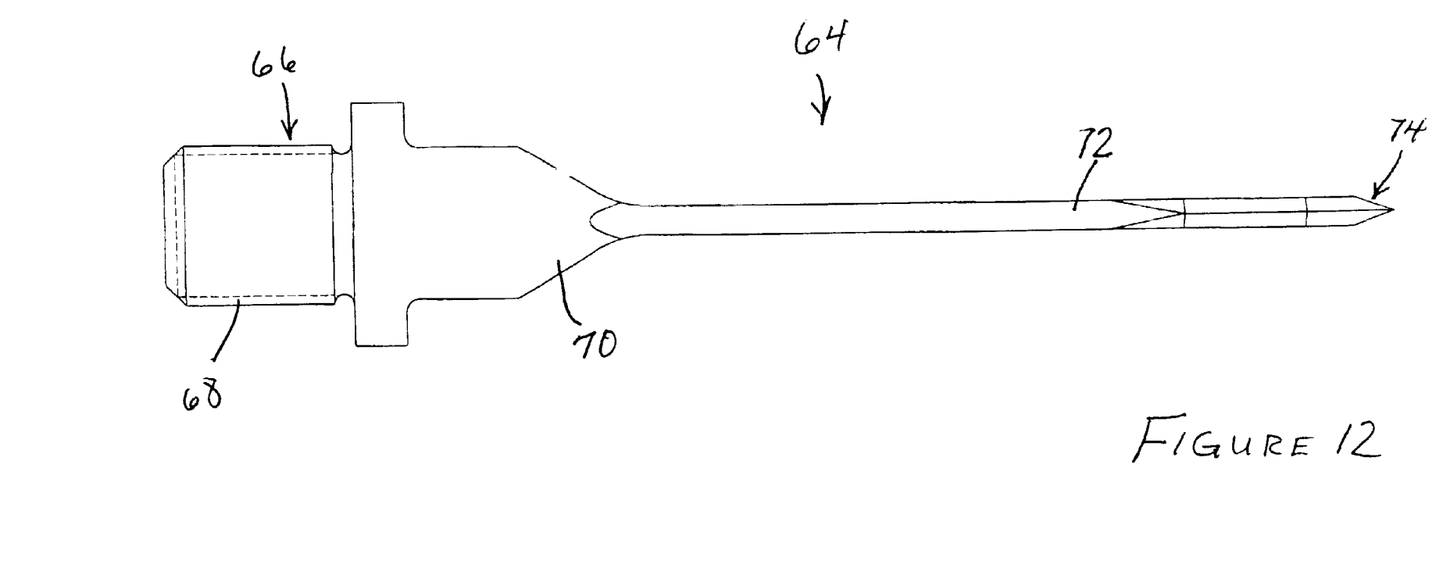
FIG. 12 is a side elevational view of the blade of FIG. 11.

As illustrated in FIG. 11, blade 64 has a tapered form, wider at shank 66 and narrowing down towards blade 74. Longitudinal edges 97 and 98 of blade 64 are colinear with respective linear blade sections 78 and 80 and are thus inclined at the same angles relative to the axis of the blade and relative to one another. The tapering of blade 64 increases the strength of the blade and reduces the incidence of failure.

Blade 64 can be operated at higher vibration amplitudes than blade 12 and thus provides a greater safety margin for the blade during a surgical operation. The fluid distribution features of blade 64 drastically reduces stresses at the tip of blade 64, in comparison with blade 12. Web sections 86 and 88 reduce stresses at the upstream and downstream ends of slot 84, thus reducing fractures between the parallel section of blade 64 and the main body or stud. In addition, tapered edges 97 and 98 reduce the overall stresses of blade 64 by decreasing the amount of vibrating mass at the blade tip. Moreover, tapered edges 97 and 98 and web sections 86 and 88 help reduce the possibility of exciting neighboring transverse (bending) frequencies. This reduction is advantageous inasmuch as such neighboring transverse frequencies generate a high pitched noise and eventually lead to failure of the blade.

Titanium appears to be the best material for bone cutting blades. It stays cool during operation, holds a good cutting edge, does not corrode and is bio-compatible. Titanium has a better strength-to-weight ratio than 17-4PH stainless steel and results in significantly fewer failures.

Although the invention has been described in terms of particular embodiments and applications, one of ordinary skill in the art, in light of this teaching, can generate additional embodiments and modifications without departing from the spirit of or exceeding the scope of the claimed invention. For example, blade 12 may be provided on opposite lateral surfaces with a pair of longitudinally extending recesses or grooves (not shown) instead of through-slot 56. Each such elongate recess or groove would communicate at an upstream end with passageway or bore 52 and would be provided at a downstream end with a circular fluid-distribution recess having an inclined surface 61 or 62.

Accordingly, it is to be understood that the drawings and descriptions herein are proffered by way of example to facilitate comprehension of the invention and should not be construed to limit the scope thereof.

What is claimed is:

1. An ultrasonic surgical blade comprising a blade body and a shank fixed at one end to said blade body and operatively connectable at an opposite end to a source of ultrasonic vibrations, said blade body having a smooth continuous cutting edge, said shank being provided with a bore for the conveyance of cooling fluid to said cutting edge, said blade body being provided with an elongate through-slot communicating at one end with said bore, said through-slot being provided with at least one web section bridging opposite sides of said through-slot so as to subdivide same into segments communicating with one another over said web section.

2. The surgical blade defined in claim 1 wherein said cutting edge is disposed in a single plane and has an arcuate section.

3. The surgical blade defined in claim 2 wherein said cutting edge includes a pair of straight sections continuous with said arcuate section at opposite ends thereof.

4. The surgical blade defined in claim 3 wherein said blade body has a longitudinal axis, said straight sections being oriented substantially parallel to said axis.

5. The surgical blade defined in claim 4 wherein said blade body is provided at an end opposite said shank with an arcuate recess communicating with said bore and extending around said through-slot at an end opposite said bore, for distributing fluid from said slot towards said cutting edge.

6. The surgical blade defined in claim 3 wherein said blade body has a longitudinal axis, said straight sections being oriented at an acute angle relative to said axis.

7. The surgical blade defined in claim 6 wherein said blade body is provided at an end opposite said shank with a recess communicating with said through-slot for distributing fluid from s aid through-slot towards said cutting edge.

8. The surgical blade defined in claim 2 wherein said arcuate section is substantially circular and is disposed on said blade body opposite said shank.

9. The surgical blade defined in claim 1 wherein said blade body is provided at an end opposite said shank with a recess communicating with said through-slot for distributing fluid from said slot towards said cutting edge.

10. The surgical blade defined in claim 9 wherein said recess is a conical or tapered cylindrical section.

11. The surgical blade defined in claim 9 wherein said recess is an annular section.

12. The surgical blade defined in claim 1 wherein said cutting edge is the only cutting edge on said blade body.

13. The surgical blade defined in claim 12 wherein said cutting edge is disposed in a single plane and has an arcuate section flanked by two linear sections.

14. The surgical blade defined in claim 1 wherein said cutting edge is free of teeth, notches, apertures, serrations, and voids.

15. An ultrasonic surgical blade comprising a blade body and a shank connected at one end to said blade body and operatively connectable at an opposite end to a source of ultrasonic vibrations, said blade body having a cutting edge, said shank being provided with a passageway or bore for the conveyance of cooling fluid to said cutting edge, said blade body being provided with an open fluid distribution channel communicating with said passageway or bore for distributing fluid therefrom along at least one lateral surface of said blade body when said blade body is disposed in tissues at a surgical site during a cutting operation, said channel including a plurality of through-slot sections traversing said blade body and communicating with one another over at least one web section defining a groove or recess for conduction of fluid from one of said through-slot sections to another thereof.

16. The surgical blade defined in claim 15 wherein said channel is provided at an end opposite said passageway or bore with at least fluid distribution guide surface for distributing fluid from said slot towards said cutting edge.

17. The surgical blade defined in claim 16 wherein said guide surface has a shape similar to a shape of said cutting edge.

18. The surgical blade defined in claim 17 wherein said cutting edge and said guide surface are circular.

19. The surgical blade defined in claim 16 wherein said guide surface has a shape of a conical or tapered cylindrical section.

20. An ultrasonic surgical blade comprising a planar blade body and a shank connected at one end to said blade body and operatively connectable at an opposite end to a source of ultrasonic vibrations, said blade body having a cutting edge and a pair of opposing major surfaces bounded in part by said cutting edge, said shank being provided with a passageway or bore for the conveyance of cooling fluid to said cutting edge, said blade body being provided with a fluid distribution guide surface communicating with said passageway or bore for distributing fluid from said passageway or bore towards said cutting edge over at least one of said major surfaces, said guide surface being a conical or tapered cylindrical section spaced from said cutting edge by a portion of said one of said major surfaces.

21. The surgical blade defined in claim 20 wherein said blade body has a planar surface between said fluid distribution guide surface and said cutting edge, said fluid distribution guide surface being an inclined surface extending between said passageway or bore and said cutting edge.

22. The surgical blade defined in claim 21 wherein said blade body is provided with a through-slot communicating at one end with said passageway or bore and at an opposite end with said recess.

\* \* \* \* \*